United States Patent [19]

Beacco et al.

[11] 4,196,288

[45] Apr. 1, 1980

[54] ERGOLINE DERIVATIVES AND A PROCESS FOR THEIR PREPARATION

[75] Inventors: Enzo Beacco, Limbiate; Luigi Bernardi, Milan; Enrico Di Salle, Milan; Giovanni Falconi, Milan; Bianca Patelli, Milan, all of Italy

[73] Assignee: Farmitalia Carlo Erba S.p.A., Milan, Italy

[21] Appl. No.: 856,536

[22] Filed: Dec. 1, 1977

[30] Foreign Application Priority Data

Dec. 6, 1976 [GB] United Kingdom ............... 50746/76

[51] Int. Cl.² .......................................... C07D 457/02
[52] U.S. Cl. ............................... 544/125; 424/248.52; 424/250; 424/248.57; 424/251; 424/261; 544/298; 544/316; 544/321; 544/361; 546/69
[58] Field of Search .................... 260/285.5, 306.8 R; 424/261; 544/125, 361, 333, 316; 546/69

Primary Examiner—Mary C. Lee
Attorney, Agent, or Firm—Stevens, Davis, Miller & Mosher

[57] ABSTRACT

New ergoline derivatives are disclosed which are compounds of formula (I) having the structure:

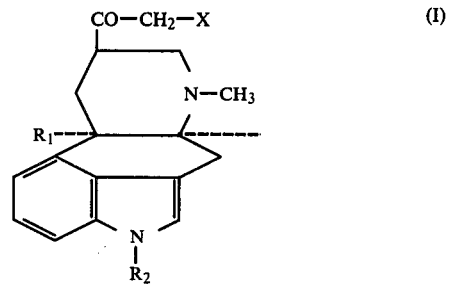

wherein $R_1$ is hydrogen or methoxy;

$R_2$ is hydrogen or methyl; and

X is hydroxy, $R_3COO$, S—$R_4$ or $NR_5R_6$ in which $R_3$ is a straight or branched alkyl having from 1 to 6 carbon atoms, unsubstituted- or substituted-phenyl, the substituents being selected from the class consisting of chlorine, bromine, alkyl or alkoxy having from 1 to 4 carbon atoms, cycloalkyl containing from 3 to 6 carbon atoms, or a heterocycle;

$R_4$ is phenyl or a heterocycle, and $R_5$ and $R_6$ are alkyl having from 1 to 4 carbon atoms, or together with the N atom to which they are attached, forming a heterocycle. The heterocycle may be a 5- or 6-membered ring which contains from 1 to 3 hetero atoms selected from the class consisting of nitrogen, oxygen and sulphur, and may be saturated or unsaturated, and unsubstituted or substituted by halogen, alkyl having from 1 to 3 carbon atoms, hydroxy, nitro, amino, $CONHNH_2$ and COOH.

22 Claims, No Drawings

ERGOLINE DERIVATIVES AND A PROCESS FOR THEIR PREPARATION

This invention relates to new ergoline derivatives and to a process for their preparation. These derivatives have the formula I:

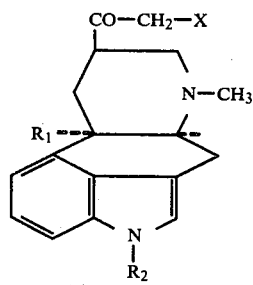

wherein $R_1$ is hydrogen or methoxy;

$R_2$ is hydrogen or methyl; and

X is hydroxy, $R_3COO$, $S-R_4$ or $NR_5R_6$ in which $R_3$ is a straight or branched alkyl having from 1 to 6 carbon atoms, unsubstituted- or substituted-phenyl, the substituents being selected from the class consisting of chlorine, bromine, alkyl or alkoxy having from 1 to 4 carbon atoms, cycloalkyl containing from 3 to 6 carbon atoms, or a heterocycle;

$R_4$ is phenyl or a heterocycle, and p $R_5$ and $R_6$ are alkyl having from 1 to 4 carbon atoms, or together with the N atom to which they are attached, forming a heterocycle.

By "heterocycle" is meant a 5- or 6-membered ring which contains from 1 to 3 hetero atoms selected from the class consisting of nitrogen, oxygen and sulphur. The heterocycle ring may be saturated or unsaturated, unsubstituted or substituted by halogen, alkyl having from 1 to 3 carbon atoms, hydroxy, nitro, amino, $CONHNH_2$ and $COOH$.

This invention also includes a process for preparing these compounds which comprises reacting a bromoketone of formula I (in which X is bromine) with an appropriate nucleophilic agent comprising a compound having a group such as $-OH$, $R_3COO-$, $R_4S-$, or $NHR_5R_6$, wherein $R_3$, $R_4$, $R_5$ and $R_6$ have the above meanings, in a solvent selected from the class consisting of methanol, ethanol, acetone, dimethylformamide and hexamethylphosphotriamide, at a temperature of from 25° to 100° C. and from 1 to 4 hours.

The products can be isolated as the free bases or as the salts of pharmaceutically acceptable acids.

The bromoketone (I, X=Br), the starting material for preparing the new compounds of Formula I, is obtained by reacting a mixed anhydride of an ergoline-8-carboxylic acid (II) with diazomethane and subsequently treating the so-obtained diazoketone (III) with hydrobromic acid. The reactions are as follows:

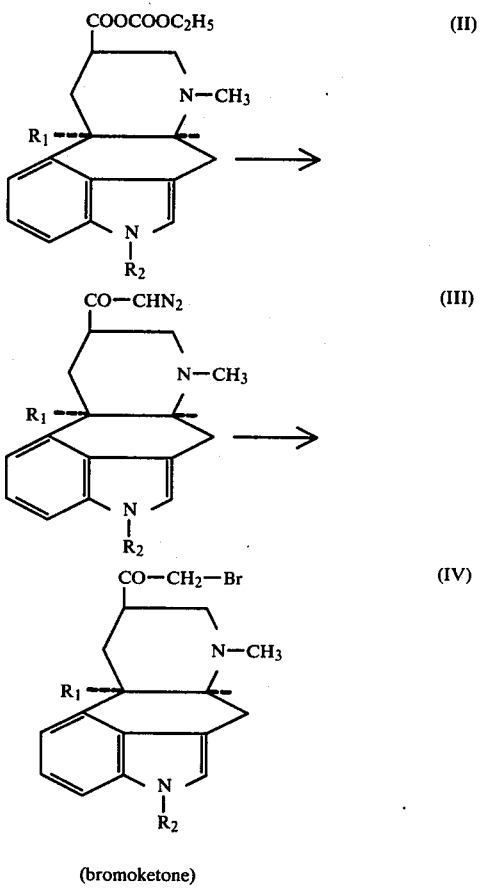

(bromoketone)

The new compounds of this invention have proved to possess a strong anti-prolactin activity in rats and a low emetic activity in dogs. Prolactin is considered to be the only hypophysial hormone involved in the maintenance of the first part of pregnancy in rats.

For the assessment of the anti-prolactin activity, the nidation inhibition test (M.C. Shelesnyak, Amer. J. Physiol., 180, 47, 1955) in rats was employed. For the ergoline derivatives this test is considered to be correlated with prolactin-inhibiting ability (K. Rezabek et al., J. Pharm. Sci., 64, 1045, 1976).

Adult female rats, of the Sprague-Dowley strain, in proestrus were mated with fertile males and their vaginal smears were examined the next morning. The presence of spermatozoa was considered evidence of impregnation and onset of pregnancy (day 1).

The compounds to be tested were administered orally or subcutaneously to groups of from six to eight rats on day 3. On day 14, the animals were sacrificed and the uterus was examined for the presence of implantation sites. The absence of implantation sites was taken as the criterion of anti-prolactin activity.

Several doses were tested for the $ED_{50}$ evaluation.

As the reference standard Bromocriptine was used, this being well known both for its anti-nidation (E. Flückiger and H. R. Wagner, Experientia, 24, 1130, 1968) and its anti-prolactin activity (C. L. Brooks and C. W. Welsch, Proc. Soc. Exp. Bio. Med., 146, 863, 1974).

The emetic activity of some of the compounds was investigated by intravenous administration to male beagle dogs weighing 15–20 kg. The animals were observed for 1 hour after treatment. Five to six animals per dose were employed for the $ED_{50}$ evaluation.

The results obtained are reported in the three tables below.

From Table 1, it appears that the new ergoline derivatives of the present invention, when administered subcutaneously, are equally or even twice as active as Bromocriptine as nidation inhibitors.

Upon oral administration (Table 2), the potency of the new derivatives is 4 to 16 times higher than that of Bromocriptine.

From Table 3, it appears that two of the ergoline derivatives of those previously listed are from 3 to 6 times less emetic than Bromocriptine in dogs.

The ratio between activity and tolerance of the new ergoline derivatives accordingly seems very high.

From the above results it is logical to predict that the new derivatives may find an advantageous clinical exploitation in the several therapeutic fields in which Bromocriptine is employed, such as inhibition of puerperal lactation, non-puerperal galactorrhoea, treatment of infertility due to hyperprolactinaemia, Parkinson's disease, or acromegaly.

The compound reference numbers given in the tables are explained in the working examples below.

TABLE 1

Nidation inhibition in rats (subcutaneous treatment)

| Compounds 335/ | $\simeq ED_{50}$ mg/kg s.c. |
|---|---|
| 615 | 0.5 |
| 1011 | 1 |
| 992 | 1 |
| 1000 | 1 |
| 1012 | 1 |
| 613 | 0.5 |
| 991 | 2 |
| 1013 | 1 |
| 611 | 1 |
| 1014 | 1 |
| Bromocriptine | 1 |

TABLE 2

Nidation inhibition in rats (oral treatment)

| Compounds 355/ | $\simeq ED_{50}$ mg/kg os |
|---|---|
| 615 | 0.5 |
| 1011 | 0.5 |
| 992 | 0.5 |
| 1000 | 0.5 |
| 1012 | 1 |
| 613 | 0.5 |
| 991 | 2 |
| 1013 | 0.5 |
| 611 | 0.5 |
| 1014 | 1 |
| Bromocriptine | 8 |

TABLE 3

Emetic activity in dogs

| Compounds 355/ | $\simeq ED_{50}$ mcg/kg i.v. |
|---|---|
| 615 | 25 |
| 613 | 45 |
| Bromocriptine | 7 |

This invention is further illustrated by the following working examples in which all temperatures are given in degrees Celsius (C.).

EXAMPLE 1

8-Bromoacetyl-6-methylergoline

To a suspension of 10.8 g of dihydrolysergic acid in 200 ml of anhydrous tetrahydrofuran containing 5.6 ml of triethylamine, 3.8 ml of ethyl chloroformate are added at $-15°$. After 6 hours the suspension is filtered and a solution of diazomethane prepared from 16 g of N-nitrosomethylurea is added. The solution is kept overnight at 10°, and then the solvent is evaporated in vacuo, the residue taken up in chloroform, washed with $Na_2CO_3$ soluton, and then water.

Evaporation of the solvent leaves a residue that is chromatographed on silica gel to give 5.8 g of diazoketone, m.p. $163°-165°$, that are dissolved in 200 ml of chloroform. Gaseous hydrobromic acid is slowly introduced into the chloroform solution until an acid reaction ensues.

The solution is warmed up on the water bath for 5 minutes, washed with $NaHCO_3$, and evaporated to dryness to give 6.4 g of 8-bromoacetyl-6-methylergoline.

EXAMPLE 2

8-Bromoacetyl-1,6-dimethylergoline

Operating as in Example 1, but using 1-methyldihydrolysergic acid, 8-bromoacetyl-1,6-dimethylergoline is obtained in 60% yield.

EXAMPLE 3

8-Bromoacetyl-10-methoxy-6-methylergoline

Operating as in Example 1, but using 10-methoxydihydrolysergic acid, 8-bromoacetyl-10-methoxy-6-methylergoline is obtained in 65% yield.

EXAMPLE 4

8-Bromoacetyl-10-methoxy-1,6-dimethylergoline

Operating as in Example 1, but using 10-methoxy-1-methyldihydrolysergic acid, 8-bromoacetyl-10-methoxy-1,6-dimethylergoline is obtained in 71% yield.

EXAMPLE 5

6-Methyl-8-(5'-bromonicotinoyloxyacetyl)ergoline (355/613)

A solution of 2.5 g of potassium 5-bromonicotinate and 2.5 g of 8-bromoacetyl-6-methylergoline in 60 ml of acetone and 40 ml of ethanol is refluxed 2 hours. The solution is filtered, evaporated to dryness, and the residue taken up in chloroform.

The chloroform solution is washed and the solvent is evaporated in vacuo to give a residue that is crystallized from acetone to give 2.6 g of 6-methyl-8-(5'-bromonicotinoyloxyacetyl)ergoline, m.p. $185°-187°$.

EXAMPLE 6

1,6-Dimethyl-(5'-bromonicotinoyloxyacetyl)ergoline (355/1020)

Operating as in Example 5, but employing 8-bromoacetyl-1,6-dimethylergoline, 1,6-dimethyl-(5'-bromonicotinoyloxyacetyl)ergoline (oil) is obtained is 60% yield.

EXAMPLE 7

10-Methoxy-6-methyl-9-(5'-bromonicotinoyloxyacetyl)ergoline (355/600)

Operating as in Example 5, but employing 10-methoxy-6-methyl-8-bromoacetylergoline, 10-methoxy-6-methyl-8-(5'-bromonicotinoyloxyacetyl)ergoline is obtained in 65% yield.

EXAMPLE 8

6-Methyl-8-acetoxyacetylergoline (355/612)

Operating as in Example 5, but employing potassium acetate, 6-methyl-8-acetoxyacetylergoline, m.p. 158°–150° is obtained in 80% yield.

EXAMPLE 9

6-Methyl-8-hydroxyacetylergoline (355/615)

A solution of 1.5 g of sodium formate and 1.5 g of 8-bromoacetyl-6-methylergoline in 60 ml of acetone and 20 ml of water is refluxed 2 hours.

The solution is evaporated to dryness, the residue is taken up in chloroform, and the organic phase is washed with a NaHCO$_3$ solution.

Evaporation of the chloroform leaves a residue that is crystallized from acetone-petroleum ether to give 0.8 g of 6-methyl-8-hydroxyacetylergoline, m.p. 202°–203°.

EXAMPLE 10

6-Methyl-8-hydroxyacetylergoline 2'-pyrrolcarboxylate (355/624)

Operating as in Example 5, but employing potassium 2-pyrrolcarboxylate, 6-methyl-8-hydroxyacetylergoline 2'-pyrrolcarboxylate, m.p. 188°–190°, is obtained in 70% yield.

EXAMPLE 11

1,6-Dimethyl-8-hydroxyacetylergoline 2'-pyrrolcarboxylate (355/632)

Operating as in Example 10, but employing 8-bromoacetyl-1,6-dimethylergoline, 1,6-dimethyl-8-hydroxyacetylergoline 2'-pyrrolcarboxylate, m.p. 198°–200°, is obtained in 55% yield.

EXAMPLE 12

8-Benzoyloxyacetyl-6-methylergoline (355/1000)

Operating as in Example 5, but employing potassium benzoate, 8-benzoyloxyacetyl-6-methylergoline, m.p. 163°–165°, is obtained in 70% yield.

EXAMPLE 13

8-Isonicotinoyloxyacetyl-6-methylergoline (355/991)

Operating as in Example 5, but employing sodium isonicotinate, 8-isonicotinoyloxyacetyl-6-methylergoline, m.p. 158°–161°, is obtained in 65% yield.

EXAMPLE 14

8-Caproyloxyacetyl-6-methylergoline (355/992)

Operating as in Example 5, but employing sodium caproate, 8-caproyloxyacetyl-6-methylergoline, m.p. 135°–137° is obtained in 58% yield.

EXAMPLE 15

8-Pivaloyloxyacetyl-6-methylergoline (355/1011)

Operating as in Example 5, but employing potassium pivalate, 8-pivaloyloxyacetyl-6-methylergoline, m.p. 155°–156°, is obtained in 80% yield.

EXAMPLE 16

8-Nicotinoyloxyacetyl-6-methylergoline (355/1012)

Operating as in Example 5, but employing sodium nicotinate, 8-nicotinoyloxyacetyl-6-methylergoline, m.p. 172°–174°, is obtained in 67% yield.

EXAMPLE 17

8-(2',6'-dimethoxybenzoyloxyacetyl)-6-methylergoline (355/1013)

Operating as in Example 5, but employing potassium 2,6-dimethoxybenzoate, 8-(2',6'-dimethoxybenzoyloxyacetyl)-6-methylergoline, m.p. 142°–146°, is obtained in 50% yield.

EXAMPLE 18

8-(2',6'-dimethylbenzoyloxyacetyl)-6-methylergoline (355/1023)

Operating as in Example 5, but employing potassium 2,6-dimethylbenzoate, 8-(2',6'-dimethylbenzoyloxyacetyl)-6-methylergoline, m.p. 184°–186°, is obtained in 55% yield.

EXAMPLE 19

6-Methyl-8-(5'-methyl-2'-pyrimidylmercapto)acetylergoline (355/1019)

A solution of 220 mg of sodium 5-methylpyrimidine-2-thiolate and 500 mg of 8-bromoacetyl-6-methylergoline in 25 ml of dimethylformamide is kept at 80° for 2 hours.

The solvent is evaporated in vacuo and the residue is chromatographed on silica-gel (eluent chloroform) to give 250 mg of 6-methyl-8-(5'-methyl-2'-pyrimidylmercapto)acetylergoline, m.p. 186°–189°.

EXAMPLE 20

6-Methyl-5-(5'-methyl-2'-1,3,4-thiazolylmercapto)-acetylergoline (355/1022)

Operating as in Example 19, but employing sodium 5-methyl-1,3,4-thiazole-2-thiolate, 6-methyl-8-(5'-methyl-2'-1,3,4-thiazolylmercapto)acetylergoline, m.p. 154°–157°, is obtained in 50% yield.

EXAMPLE 21

6-Methyl-8-morpholinoacetylergoline (355/614)

A solution of 0.9 g of 8-bromoacetyl-6-methylergoline and 1 ml of morpholine in 20 ml of ethanol is kept at room temperature for 1 hour.

The solvent is evaporated in vacuo, the residue is taken up in chloroform and the chloroform extract is washed with 2N NaOH, and then with water.

Evaporation of the solvent in vacuo leaves a residue that is crystallized from acetone-petroleum ether to give 0.7 g of 6-methyl-8-morpholinoacetylergoline, m.p. 178°–180°.

EXAMPLE 22

1,6-Dimethyl-8-morpholinoacetylergoline (355/633)

Operating as in Example 21, but employing 8-bromoacetyl-1,6-dimethylergoline, 1,6-dimethyl-8-morpholinoacetylergoline is obtained in 45% yield, characterized as the maleate, m.p. 198°–200°.

EXAMPLE 23

6-Methyl-8-diethylaminoacetylergoline, (355/625)

Operating as in Example 21, but employing diethylamine, 6-methyl-8-diethylaminoacetylergoline m.p. 189°–191°, is obtained in 60% yield

EXAMPLE 24

6-Methyl-8-piperidinoacetylergoline (355/611)

Operating as in Example 21, but employing piperidine, 6-methyl-8-piperidinoacetylergoline, m.p. 168°–170°, is obtained in 70% yield.

EXAMPLE 25

6-Methyl-8-(4'-methylpiperazino)acetylergoline (355/1014)

Operating as in Example 21, but employing 4-methylpiperazine, 6-methyl-b 8-(4'-methylpiperazino)acetylergoline, m.p. 198°–202°, is obtained in 72% yield.

What is claimed is:
1. A compound selected from the class consisting of:
(a) 6-methyl-8-(5'-bromonicotinoyloxyacetyl)-ergoline;
(b) 1,6-dimethyl-(5'-bromonicotinoyloxyacetyl)-ergoline;
(c) 10-methoxy-6-methyl-8-(5'-bromonicotinoyloxyacetyl)-ergoline;
(d) 6-methyl-8-acetoxyacetylergoline;
(e) 6-methyl-8-hydroxyacetylergoline;
(f) 6-methyl-8-hydroxyacetylergoline-2'-pyrrolcarboxylate;
(g) 1,6-dimethyl-8-hydroxyacetylergoline-2'-pyrrolcarboxylate;
(h) 8-benzoyloxyacetyl-6-methylergoline;
(i) 8-isonicotinoyloxyacetyl-6-methylergoline;
(j) 8-caproyloxyacetyl-6-methylergoline;
(k) 8-pivaloyloxyacetyl-6-methylergoline;
(l) 8-nicotinoyloxyacetyl-6-methylergoline;
(m) 8-(2',6'-dimethoxybenzoyloxyacetyl)-6-methylergoline;
(n) 8-(2',6'-dimethylbenzoyloxyacetyl)-6-methylergoline;
(o) 6-methyl-8-(5'-methyl-2'-pyrimidylmercapto)-acetylergoline;
(p) 6-methyl-8-(5'-methyl-2'-1,3,4-thiazolylmercapto)-acetylergoline;
(q) 6-methyl-8-morpholinoacetylergoline;
(r) 1,6-dimethyl-8-morpholinoacetylergoline;
(s) 6-methyl-8-diethylaminoacetylergoline;
(t) 6-methyl-8-piperidinoacetylergoline;
(u) 6-methyl-8-(4'-methylpiperazino)acetylergoline.

2. The compound as defined in claim 1, which is 6-methyl-8-(5'-bromonicotinoyloxyacetyl)-ergoline.

3. The compound as defined in claim 1, which is 1,6-dimethyl-(5'-bromonicotinoyloxyacetyl)-ergoline.

4. The compound as defined in claim 1, which is 10-methoxy-6-methyl-8-(5'-bromonicotinoyloxyacetyle)-ergoline.

5. The compound as defined in claim 1, which is 6-methyl-8-aceotxyacetylergoline.

6. The compound as defined in claim 1, which is 6-methyl-8-hydroxyacetylergoline.

7. The compound as defined in claim 1, which is 6-methyl-8-hydroxyacetylergoline 2'-pyrrolcarboxylate.

8. The compound as defined in claim 1, which is 1,6-dimethyl-8-hydroxyacetylergoline 2'-pyrrolcarboxylate.

9. The compound as defined in claim 1, which is 8-benzoyloxyacetyl-6-methylergoline.

10. The compound as defined in claim 1, which is 8-isonicotinoyloxyacetyl-6-methylergoline.

11. The compound as defined in claim 1, which is 8-caproyloxyacetyl-6-methylergoline.

12. The compound as defined in claim 1, which is 8-pivaloyloxyacetyl-6-methylergoline.

13. The compound as defined in claim 1, which is 8-nicotinoyloxyacetyl-6-methylergoline.

14. The compound as defined in claim 1, which is 8-(2',6'-dimethoxybenzoyloxyacetyl)-6-methylergoline.

15. The compound as defined in claim 1, which is 8-(2',6'-dimethylbenzoyloxyacetyl)-6-methylergoline.

16. The compound as defined in claim 1, which is 6-methyl-8-(5'-methyl-2'-pyrimidylmercapto)-acetylergoline.

17. The compound as defined in claim 1, which is 6-methyl-8-(5'-methyl-2'-1,3,4-thiazolylmercapto)-acetylergoline.

18. The compound as defined in claim 1, which is 6-methyl-8-morpholinoacetylergoline.

19. The compound as defined in claim 1, which is 1,6-dimethyl-8-morpholinoacetylergoline.

20. The compound as defined in claim 1, which is 6-methyl-8-diethylaminoacetylergoline.

21. The compound as defined in claim 1, which is 6-methyl-8-piperidinoacetylergoline.

22. The compound as defined in claim 1, which is 6-methyl-8-(4'-methylpiperazino)acetylergoline.

* * * * *

UNITED STATES PATENT AND TRADEMARK OFFICE
CERTIFICATE OF CORRECTION

PATENT NO. : 4,196,288
DATED : April 1, 1980
INVENTOR(S) : Enzo BEACCO et al

It is certified that error appears in the above-identified patent and that said Letters Patent are hereby corrected as shown below:

In the five structural formulae shown in the Abstract and in columns 1 and 2, for the dashed line directly opposite $R_1$ --- read in each instance a solid line.

Column 5, Example 7, title compound, for "10-Methoxy-6-methyl-9-" read -- 10-Methoxy-6-methyl-8 --

Column 6, Example 20, title compound, for "6-Methyl-5-" read -- 6-Methyl-8- --

Column 7, Example 25, line 2, for "6-methyl-b" read -- 6-methyl-8- --

Column 8, claim 5, line 2, read -- acetoxyacetylergoline --

Signed and Sealed this

Twenty-first Day of October 1980

[SEAL]

Attest:

Attesting Officer

SIDNEY A. DIAMOND

Commissioner of Patents and Trademarks